United States Patent
Weaver et al.

(10) Patent No.: US 9,933,079 B2
(45) Date of Patent: Apr. 3, 2018

(54) STACKED MEMBRANE FOR PRESSURE ACTUATED VALVE

(75) Inventors: Karla Weaver, Framingham, MA (US); Paul DiCarlo, Middleboro, MA (US)

(73) Assignee: AngioDynamics, Inc., Latham, NY (US)

( * ) Notice: Subject to any disclaimer, the term of this patent is extended or adjusted under 35 U.S.C. 154(b) by 1171 days.

(21) Appl. No.: 10/768,629

(22) Filed: Jan. 29, 2004

(65) Prior Publication Data

US 2005/0171490 A1    Aug. 4, 2005

(51) Int. Cl.
| | |
|---|---|
| *A61M 5/00* | (2006.01) |
| *F16K 15/14* | (2006.01) |
| *A61M 39/02* | (2006.01) |
| *A61M 39/24* | (2006.01) |
| *F16K 17/18* | (2006.01) |

(52) U.S. Cl.
CPC ........... *F16K 15/147* (2013.01); *A61M 39/02* (2013.01); *A61M 39/24* (2013.01); *F16K 17/18* (2013.01); *A61M 2039/242* (2013.01); *A61M 2039/2426* (2013.01)

(58) Field of Classification Search
CPC ............ A61M 39/24; A61M 2039/242; A61M 2039/2426
USPC ...... 604/167.01–167.04, 236–237, 246–247, 604/533–537
See application file for complete search history.

(56) References Cited

U.S. PATENT DOCUMENTS

| | | | |
|---|---|---|---|
| 2,446,571 A | 3/1944 | Browne | |
| 2,720,881 A | 10/1955 | Weaver et al. | |
| 2,755,060 A | 7/1956 | Twyman | |
| 3,113,586 A | 12/1963 | Edmark, Jr. | |
| 3,159,175 A * | 12/1964 | MacMillan | 137/493 |
| 3,477,438 A | 11/1969 | Allen et al. | |
| 3,514,438 A | 5/1970 | Nelsen et al. | |

(Continued)

FOREIGN PATENT DOCUMENTS

| | | |
|---|---|---|
| DE | 20208420 | 10/2002 |
| EP | 0128525 | 12/1984 |

(Continued)

OTHER PUBLICATIONS

Asch, "Venous access: options, approaches and issues," Can Assoc. Radiol J., vol. 52, No. 3 pp. 153-164 (2001).

(Continued)

*Primary Examiner* — Emily Schmidt

(74) *Attorney, Agent, or Firm* — Peter Flora, Esq.

(57) ABSTRACT

A pressure activated valve for medical applications comprises a housing having a lumen extending therethrough from a proximal end to a distal end thereof and a flow control membrane extending across the lumen to control flow therethrough, the flow control membrane including a mounting portion at which the flow control membrane is coupled to the housing and a lumen occluding portion having a slit extending therethrough so that, when the lumen occluding portion is subjected to a pressure of at least a predetermined threshold level, the lumen occluding portion moves from a closed configuration in which flow through the lumen is prevented to an open configuration in which flow is permitted and wherein a thickness of the mounting portion is greater than a thickness of the lumen occluding portion.

13 Claims, 3 Drawing Sheets

(56) References Cited

U.S. PATENT DOCUMENTS

| | | |
|---|---|---|
| 3,525,357 A | 8/1970 | Koreski |
| 3,621,557 A | 11/1971 | Cushman et al. |
| 3,669,323 A | 6/1972 | Harker et al. |
| 3,673,612 A | 7/1972 | Merrill et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,941,149 A | 3/1976 | Mittleman |
| 3,955,594 A | 5/1976 | Snow |
| 4,072,146 A | 2/1978 | Howes |
| 4,142,525 A | 3/1979 | Binard et al. |
| 4,143,853 A | 3/1979 | Abramson |
| 4,244,379 A | 1/1981 | Smith |
| 4,387,879 A | 6/1983 | Tauschinski |
| 4,405,316 A | 9/1983 | Mittleman |
| 4,434,810 A | 3/1984 | Atkinson |
| 4,447,237 A | 5/1984 | Frisch et al. |
| 4,468,224 A | 8/1984 | Enzmann et al. |
| 4,502,502 A | 3/1985 | Krug |
| 4,524,805 A | 6/1985 | Hoffman |
| 4,543,087 A | 9/1985 | Sommercorn et al. |
| 4,552,553 A | 11/1985 | Schulte et al. |
| 4,610,665 A | 9/1986 | Matsumoto et al. |
| 4,616,768 A | 10/1986 | Flier |
| 4,646,945 A | 3/1987 | Steiner et al. |
| 4,673,393 A | 6/1987 | Suzuki et al. |
| 4,681,572 A | 7/1987 | Tokarz et al. |
| 4,692,146 A | 9/1987 | Hilger |
| 4,722,725 A | 2/1988 | Sawyer et al. |
| 4,790,832 A | 12/1988 | Lopez |
| 4,798,594 A | 1/1989 | Hillstead |
| 4,801,297 A | 1/1989 | Mueller |
| 4,908,028 A | 3/1990 | Richmond |
| 4,944,726 A | 7/1990 | Hilal et al. |
| 4,946,448 A | 8/1990 | Richmond |
| 4,960,412 A | 10/1990 | Fink |
| 5,000,745 A | 3/1991 | Guest et al. |
| 5,009,391 A | 4/1991 | Steigerwald |
| 5,030,210 A | 7/1991 | Alchas et al. |
| 5,084,015 A | 1/1992 | Moriuchi |
| 5,098,405 A | 3/1992 | Peterson et al. |
| 5,125,893 A | 6/1992 | Dryden |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,176,662 A * | 1/1993 | Bartholomew et al. ...... 604/513 |
| 5,201,722 A | 4/1993 | Moorehead et al. |
| 5,205,834 A | 4/1993 | Moorehead et al. |
| 5,249,598 A | 10/1993 | Schmidt |
| 5,254,086 A | 10/1993 | Moorehead et al. |
| 5,324,274 A | 6/1994 | Martin |
| 5,330,424 A | 7/1994 | Palmer et al. |
| 5,336,203 A | 8/1994 | Goldhardt et al. |
| 5,360,407 A | 11/1994 | Leonard et al. |
| 5,370,624 A | 12/1994 | Edwards et al. |
| 5,395,352 A | 3/1995 | Penny |
| 5,396,925 A | 3/1995 | Poli et al. |
| 5,399,168 A | 3/1995 | Wadsworth et al. |
| 5,401,255 A | 3/1995 | Sutherland et al. |
| D357,735 S | 4/1995 | McPhee |
| 5,405,340 A | 4/1995 | Fageol et al. |
| 5,411,491 A | 5/1995 | Goldhardt et al. |
| 5,453,097 A | 9/1995 | Paradis |
| 5,454,784 A | 10/1995 | Atkinson et al. |
| 5,469,805 A | 11/1995 | Gibbs et al. |
| 5,470,305 A | 11/1995 | Arnett et al. |
| 5,484,420 A | 1/1996 | Russo |
| 5,575,769 A | 1/1996 | Vaillancourt et al. |
| 5,542,923 A | 8/1996 | Ensminger et al. |
| 5,545,150 A | 8/1996 | Danks et al. |
| 5,554,136 A | 9/1996 | Luther |
| 5,562,618 A | 10/1996 | Cai et al. |
| 5,571,093 A | 11/1996 | Cruz et al. |
| 5,619,393 A | 4/1997 | Summerfelt et al. |
| 5,624,395 A | 4/1997 | Mikhail et al. |
| 5,637,099 A | 6/1997 | Durdin et al. |
| 5,667,500 A | 9/1997 | Palmer et al. |
| 5,707,357 A | 1/1998 | Mikhail et al. |
| 5,743,873 A | 4/1998 | Cai et al. |
| 5,743,884 A * | 4/1998 | Hasson et al. ........... 604/167.02 |
| 5,743,894 A | 4/1998 | Swisher |
| 5,752,938 A | 5/1998 | Flatland et al. |
| 5,803,078 A | 9/1998 | Brauner |
| 5,807,349 A | 9/1998 | Person et al. |
| 5,810,789 A | 9/1998 | Powers et al. |
| 5,843,044 A | 12/1998 | Moorehead |
| 5,853,397 A | 12/1998 | Shemesh et al. |
| 5,865,308 A | 2/1999 | Qin et al. |
| 5,944,698 A * | 8/1999 | Fischer et al. ................. 604/236 |
| 5,984,902 A * | 11/1999 | Moorehead ................... 604/247 |
| 5,989,233 A | 11/1999 | Yoon |
| 6,033,393 A | 3/2000 | Balbierz et al. |
| 6,045,734 A | 4/2000 | Luther et al. |
| 6,050,934 A | 4/2000 | Mikhail et al. |
| 6,056,717 A | 5/2000 | Finch et al. |
| 6,062,244 A | 5/2000 | Arkans |
| 6,092,551 A | 7/2000 | Bennett |
| 6,099,505 A | 8/2000 | Ryan et al. |
| 6,120,483 A | 9/2000 | Davey et al. |
| 6,152,909 A | 11/2000 | Bagaoisan et al. |
| 6,210,366 B1 | 4/2001 | Sanfilippo |
| 6,227,200 B1 | 5/2001 | Crump et al. |
| 6,270,489 B1 | 8/2001 | Wise et al. |
| 6,306,124 B1 | 10/2001 | Jones et al. |
| 6,364,861 B1 | 4/2002 | Feith et al. |
| 6,364,867 B2 | 4/2002 | Wise et al. |
| 6,375,637 B1 | 4/2002 | Campbell et al. |
| 6,436,077 B1 | 8/2002 | Davey et al. |
| 6,442,415 B1 | 8/2002 | Bis et al. |
| 6,446,671 B2 | 9/2002 | Armenia et al. |
| 6,508,791 B1 | 1/2003 | Guerrero |
| 6,551,270 B1 | 4/2003 | Bimbo et al. |
| 6,610,031 B1 | 8/2003 | Chin |
| 6,726,063 B2 | 4/2004 | Stull et al. |
| 6,786,884 B1 | 9/2004 | DeCant et al. |
| 6,874,999 B2 | 4/2005 | Dai et al. |
| 6,953,450 B2 | 10/2005 | Baldwin et al. |
| 6,994,314 B2 | 2/2006 | Garnier et al. |
| 7,081,106 B1 | 7/2006 | Guo et al. |
| 7,252,652 B2 | 8/2007 | Moorehead et al. |
| 7,291,133 B1 | 11/2007 | Kindler et al. |
| 7,316,655 B2 | 1/2008 | Garibotto et al. |
| 7,435,236 B2 | 10/2008 | Weaver et al. |
| 7,601,141 B2 | 10/2009 | Dikeman et al. |
| 7,637,893 B2 | 12/2009 | Christensen et al. |
| 7,758,541 B2 | 7/2010 | Wallace et al. |
| 2001/0023333 A1 | 9/2001 | Wisse et al. |
| 2001/0037079 A1 | 11/2001 | Burbank et al. |
| 2002/0010425 A1 | 1/2002 | Guo et al. |
| 2002/0016584 A1 | 2/2002 | Wise et al. |
| 2002/0121530 A1 | 9/2002 | Socier |
| 2002/0156430 A1* | 10/2002 | Haarala et al. ............... 604/247 |
| 2002/0165492 A1 | 11/2002 | Davey et al. |
| 2002/0193752 A1 | 12/2002 | Lynn |
| 2003/0122095 A1* | 7/2003 | Wilson et al. ................... 251/12 |
| 2004/0034324 A1 | 2/2004 | Seese et al. |
| 2004/0064128 A1 | 4/2004 | Raijman et al. |
| 2004/0102738 A1 | 5/2004 | Dikeman |
| 2004/0108479 A1 | 6/2004 | Garnier et al. |
| 2004/0186444 A1 | 9/2004 | Daly et al. |
| 2004/0193119 A1 | 9/2004 | Canaud et al. |
| 2004/0210194 A1 | 10/2004 | Bonnette et al. |
| 2004/0267185 A1 | 12/2004 | Weaver et al. |
| 2005/0010176 A1 | 1/2005 | Dikeman et al. |
| 2005/0027261 A1 | 2/2005 | Weaver et al. |
| 2005/0043703 A1 | 2/2005 | Nordgren |
| 2005/0049555 A1 | 3/2005 | Moorehead et al. |
| 2005/0149116 A1 | 7/2005 | Edwards et al. |
| 2005/0171490 A1 | 8/2005 | Weaver et al. |
| 2005/0171510 A1 | 8/2005 | DiCarlo et al. |
| 2005/0283122 A1 | 12/2005 | Nordgren |

(56) References Cited

U.S. PATENT DOCUMENTS

| | | |
|---|---|---|
| 2006/0129092 A1 | 6/2006 | Hanlon et al. |
| 2006/0135949 A1 | 6/2006 | Rome et al. |
| 2006/0149211 A1 | 7/2006 | Simpson et al. |
| 2007/0161940 A1 | 7/2007 | Blanchard et al. |
| 2007/0161970 A1 | 7/2007 | Moorehead et al. |
| 2007/0276313 A1 | 11/2007 | Moorehead et al. |
| 2008/0108956 A1 | 5/2008 | Lynn et al. |
| 2009/0292252 A1 | 11/2009 | Lareau et al. |

FOREIGN PATENT DOCUMENTS

| | | |
|---|---|---|
| EP | 0337617 | 10/1989 |
| EP | 0366814 | 5/1990 |
| EP | 0 474 069 | 3/1992 |
| EP | 0864336 | 9/1998 |
| EP | 0930082 | 7/1999 |
| EP | 1016431 | 7/2000 |
| FR | 2508008 | 12/1982 |
| FR | 2718969 | 10/1995 |
| GB | 966137 | 8/1964 |
| GB | 2 102 398 | 2/1983 |
| JP | 59133877 | 8/1984 |
| JP | 63255057 | 10/1988 |
| JP | 9038197 | 2/1997 |
| WO | WO-89/002764 | 4/1989 |
| WO | WO-91/012838 | 9/1991 |
| WO | 92/06732 | 4/1992 |
| WO | 95/16480 | 6/1995 |
| WO | WO-96/017190 | 6/1996 |
| WO | WO-96/023158 | 8/1996 |
| WO | WO-96/041649 | 12/1996 |
| WO | 97/23255 | 7/1997 |
| WO | 97/26931 | 7/1997 |
| WO | WO-98/022178 | 5/1998 |
| WO | 99/42166 | 8/1999 |
| WO | WO-00/006230 | 2/2000 |
| WO | 00/44419 | 8/2000 |
| WO | WO-01/074434 | 10/2001 |
| WO | 03/084832 | 10/2003 |
| WO | 2005/023355 | 3/2005 |
| WO | WO-08/089985 | 7/2008 |

OTHER PUBLICATIONS

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

Office Action dated Jun. 30, 2011 for Canadian Patent Application No. 2,553,331 (2 pages).

Extended Search Report dated May 19, 2011 for European Patent Application No. 11158827.3 (6 pages).

Examination Report dated Apr. 27, 2010 for European Patent Application No. 05705428.0 (3 pages).

International Search Report and Written Opinion dated Apr. 12, 2005 for International Application No. PCT/US2005/000761 (10 pages).

International Preliminary Report on Patentability dated Jul. 31, 2006 for International Application No. PCT/US2005/000761 (8 pages).

* cited by examiner

STACKED MEMBRANE FOR PRESSURE ACTUATED VALVE

The present application incorporates by reference the entire disclosure of (1) U.S. application Ser. No. 10/768,565 entitled "Pressure Activated Safety Valve With High Flow Slit" filed on Jan. 29, 2004 naming Karla Weaver and Paul DiCarlo as inventors; (2) U.S. application Ser. No. 10/768,571 entitled "Pressure Activated Safety Valve With Anti-Adherent Coating" filed on Jan. 29, 2004 naming Karla Weaver and Paul DiCarlo as inventors; (3) U.S. application Ser. No. 10/768,855 entitled "Pressure Actuated Safety Valve With Spiral Flow Membrane" filed on Jan. 29, 2004 naming Karla Weaver and Paul DiCarlo as inventors; and (4) U.S. application Ser. No. 10/768,479 entitled "Dual Well Port Device" filed on Jan. 29, 2004 naming Katie Daly, Kristian DiMatteo and Eric Houde as inventors.

BACKGROUND OF THE INVENTION

Many medical procedures require repeated and prolonged access to a patient's vascular system. For example, during dialysis treatment blood may be removed from the body for external filtering and purification, to make up for the inability of the patient's kidneys to carry out that function. In this process, the patient's venous blood is extracted, processed in a dialysis machine and returned to the patient. The dialysis machine purifies the blood by diffusing harmful compounds through membranes, and may add to the blood therapeutic agents, nutrients etc., as required before returning it to the patient's body. Typically the blood is extracted from a source vein (e.g., the vena cava) through a catheter sutured to the skin with a distal needle of the catheter penetrating the source vein.

It is impractical and dangerous to insert and remove the catheter for each dialysis session. Thus, the needle and catheter are generally implanted semi permanently with a distal portion of the assembly remaining within the patient in contact with the vascular system while a proximal portion of the catheter remains external to the patient's body. The proximal end is sealed after each dialysis session has been completed to prevent blood loss and infections. However, even small amounts of blood oozing into the proximal end of the catheter may be dangerous as thrombi can form therein due to coagulation. These thrombi may then be introduced into the patient's vascular system when blood flows from the dialysis machine through the catheter in a later session.

A common method of sealing the catheter after a dialysis session is to shut the catheter with a simple clamp. This method is often unsatisfactory because the repeated application of the clamp may weaken the walls of the catheter due to the stress placed on the walls at a single point. In addition, the pinched area of the catheter may not be completely sealed allowing air to enter the catheter which may coagulate any blood present within the catheter. Alternatively, valves have been used at the opening of the catheter in an attempt to prevent leaking through the catheter when the dialysis machine is disconnected. However, the unreliability of conventional valves has rendered them unsatisfactory for extended use.

One type of valve that is often used in sealing catheters is the Pressure Activated Safety Valve (PASV), which opens in response to a prescribed pressure being applied to the fluid flowing in the catheter. When no pressure is applied, the PASV remains closed, thus sealing the catheter. These valves are subject to great mechanical stress due to the high number of open-close cycles they undergo, and to the high flow of fluids (such as blood) they must pass. The valves are designed to reliably seal the catheter opening when not in use, while retaining a simple and relatively inexpensive configuration.

SUMMARY OF THE INVENTION

In one aspect, the present invention is directed to a pressure activated valve for medical applications comprising a housing having a lumen extending therethrough from a proximal end to a distal end thereof and a flow control membrane extending across the lumen to control flow therethrough, the flow control membrane including a mounting portion at which the flow control membrane is coupled to the housing and a lumen occluding portion having a slit extending therethrough so that, when the lumen occluding portion is subjected to a pressure of at least a predetermined threshold level, the lumen occluding portion moves from a closed configuration in which flow through the lumen is prevented to an open configuration in which flow is permitted and wherein a thickness of the mounting portion is greater than a thickness of the lumen occluding portion.

The present invention is further directed to a method of forming a membrane for a pressure activated valve, comprising the steps of forming a substantially planar flow control membrane dimensioned to fit in a housing of the pressure activated valve, wherein a mounting portion of the flow control membrane is adapted to engage the housing and forming at least one slit in the flow control membrane, the slit being openable by pressure of a fluid in the pressure activated valve of at least a predetermined threshold level in combination with the steps of forming an annular base membrane dimensioned to substantially overlie the mounting portion of the flow control membrane and stacking the base membrane on the mounting portion of the flow control membrane.

DETAILED DESCRIPTION

Figure 1:
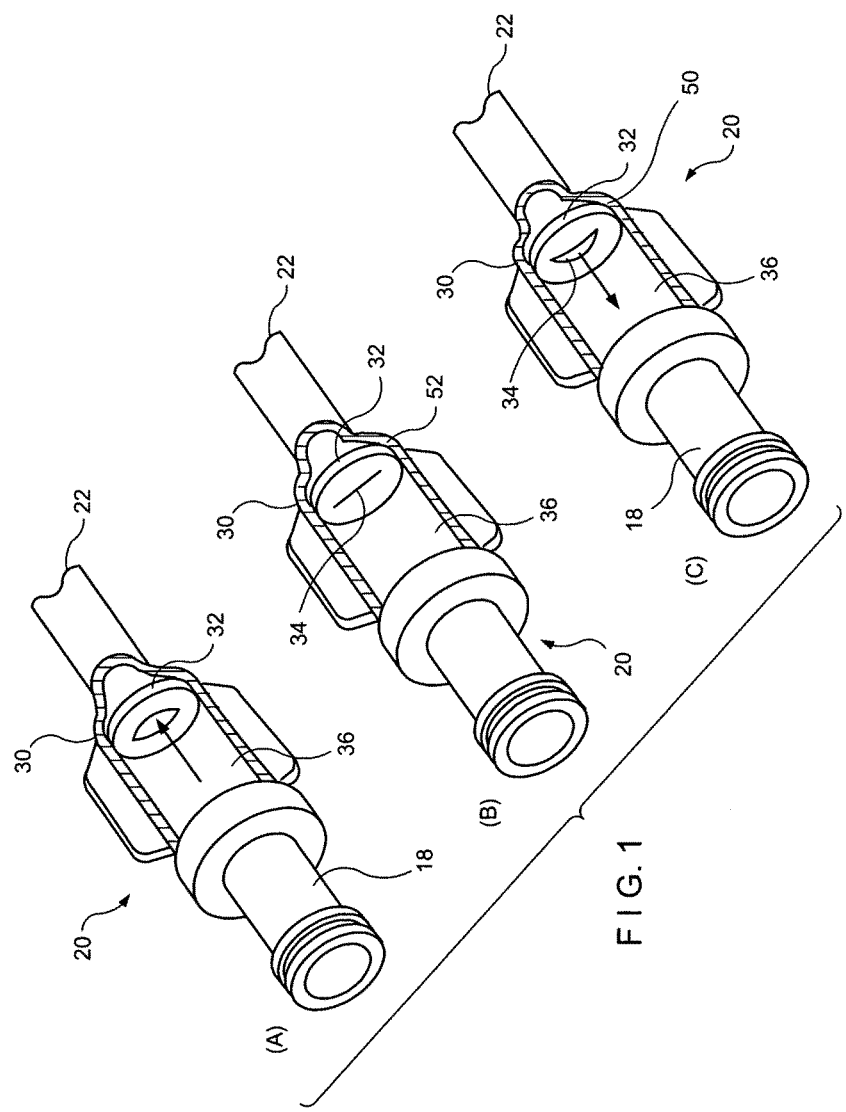
FIG. 1 is a diagram showing a pressure activated safety valve in a closed configuration and in two opposite flow configurations.

The present invention may be further understood with reference to the following description and the appended drawings, wherein like elements are referred to with the same reference numerals. The invention is related to the field of medical valves, and more specifically to the field of pressure activated valves that are used to seal a lumen of a medical catheter.

Semi-permanently placed catheters may be useful for a variety of medical procedures which require repeated access to a patient's vascular system in addition to the dialysis treatments mentioned above. For example, chemotherapy infusions may be repeated several times a week for extended periods of time. For safety reasons, as well as to improve the comfort of the patient, injections of these therapeutic agents may be better carried out with an implantable, semi-permanent vascular access catheter. Many other conditions that require chronic venous supply of therapeutic agents, nutrients, blood products or other fluids to the patient may also benefit from implantable access catheters, to avoid repeated insertion of a needle into the patient's blood vessels. Thus, although the following description focuses on dialysis, those skilled in the art will understand that the invention may be used in conjunction with any of a wide variety of procedures which require long term implantation of catheters within the body.

Examples of such implantable catheters include those manufactured by Vaxcel™, such as the Chronic Dialysis Catheter and the Implantable Vascular Access System. These devices typically are inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations. These catheters may include two or more lumens which are used respectively to remove fluids from and to reintroduce to the blood vessel. When the catheter is disconnected from the dialysis machine, it can be left within the patient, connected to the patient's vascular system. In that case, it is important to securely seal the hub of the catheter to prevent fluids from escaping and contaminants from entering the patient's body. If a seal is not obtained, the patient incurs serious risks such as the possibility of infections, the risk of embolisms due to air entering the blood stream and the risk of venous thrombosis due to coagulation of blood in and near the catheter. Leakage from an improperly sealed catheter can expose the attending medical staff to a risk of infection by blood borne pathogens. Thus a mechanism is necessary to ensure that the proximal end of the catheter can be sealed when it is not in use.

A conventional clamp or a clip can be used to seal the catheter between medical sessions, but several drawbacks exist with this method. For example, the material of the catheter wall can be damaged by the clamp, since the sealing force is exerted on a very small surface area of the catheter. Repeatedly clamping and releasing the catheter may, over time, weaken the material sufficiently to cause a failure of the catheter. This is dangerous for the patient, since it can lead to loss of blood and to infection. A sealing clamp may also become dislodged during activities of the patient, thus increasing the risk of leaks, infections, and various other problems listed above. Placing a clamp on the catheter's proximal end may also increase the bulk of the device which is exposed outside the patient's body, and may adversely affect patient comfort.

An alternative to clamping the catheter's proximal end is to include self sealing valves near the entrance of the flow passages of the catheter, to seal those passages when not used. For example, one or more valves may be placed in the catheter (e.g., near a proximal end thereof. The valves are preferably designed to seal the catheter's lumen under certain conditions, and to allow passage of a fluid under other conditions. In an exemplary case applicable to a dialysis catheter, the system of valves may seal the catheter when it is not connected to an operating dialysis machine, and may allow both an outflow of non-purified blood and an inflow of purified blood to the patient when an operating dialysis machine is connected thereto. The valves used in dialysis thus selectively allow bidirectional flow into the patient and out of the patient, depending on the pressures applied thereto.

Pressure activated safety valves (PASV's) are one type of flow control device that is often used to seal such semi-permanently implanted vascular catheters when not in use. These valves function by opening when subject to a predetermined flow pressure, and by remaining closed when subject to pressures less than the predetermined flow pressure. In the exemplary case of a PASV used in a dialysis catheter, the valve may be set to open when subject to a pressure which would be applied thereto by an operating dialysis machine and to remain closed when subject to lesser pressures (e.g., pressures applied by the vascular system itself. When a dialysis machine is not connected thereto (or when a connected dialysis machine is not operating), the pressure in the lumen is insufficient to open the PASV, and the dialysis catheter remains sealed. The PASV may be calibrated such that the pressure due to the blood flowing naturally through the patient's vascular system is not sufficient to open it and unseal the catheter.

FIGS. 1A-1C show cutaway views of a PASV 20 (a three-way safety valve), depicting three flow conditions. In condition A, a fluid is introduced into the catheter 22 via a hub 18. In condition C, fluid is removed from the catheter 22 through the hub 18, and in condition B the valve is closed and no fluid flows therethrough. In the context of a dialysis catheter, condition A is infusion, i.e., blood is traveling from the dialysis machine to the patient and condition C is aspiration, i.e., blood is traveling from the patient to the dialysis machine. Condition B corresponds to a closed state where the valve membrane is in the closed position allowing no fluid travel, e.g., a condition in which no dialysis treatment is ongoing so that the valve 20 remains in the closed configuration. The closed position prevents bleedback. According to one exemplary embodiment of the present invention, the valve 20 comprises a valve housing 30 forming a body of the device and a flow control membrane 32 disposed within the housing 30. The hub 18 may define the valve housing 30 or, alternatively, the housing 30 and the hub 18 may be formed as separate units. A fluid flow chamber 36 extends through the housing 30 so that fluid (e.g., blood) may flow therethrough into and out of the catheter 22. As would be understood by those of skill in the art, although the exemplary flow chamber 36 is shown as substantially cylindrical, in different applications the flow chamber 36 may be of any other shape suitable for the efficient flow of a fluid. The housing 30 may be connected to a medical device (for example a dialysis machine) on a proximal side and to a patient line (for example a dialysis catheter) on the distal side.

A flow control membrane 32 may be disposed in the flow chamber 36 positioned to selectively impede the passage of fluid though flow chamber 36. The flow control membrane may, for example, be located adjacent the proximal end of the housing 30. One or more slits 34 are extended through the membrane 32 so that under predetermined conditions, the slit 34 opens. When the membrane 32 is not subject to the predetermined conditions, the slit 34 remains closed. For example, the flow control membrane 32 may be constructed so that the slit 34 opens when subject to a flow pressure of at least a predetermined threshold level, but remains securely closed when a flow pressure impinging thereon is less than this threshold level. This threshold valve opening pressure may correspond, for example, to pressures to which the valve would be subjected if an operating dialysis machine were connected thereto and will preferably be substantially greater than pressure to which the membrane 32 would be generated by the patient's vascular system or which would be induced in the housing 30 due to patient activity.

The valve 20 is therefore expressly designed so that the pressure imparted thereto through the operation of a dialysis machine will open the slit 34 and allow a desired volumetric flow of blood to pass through between the proximal and distal ends of the housing to and from the dialysis machine and the patient's vascular system. For example, membrane 32 is formed so that, when not subject to a pressure of at least the threshold level, edges of the slit 34 remain joined. A first exemplary embodiment may be a 0.010 inch membrane sandwiched between two membranes having a thickness of 0.0025 inches. A second exemplary embodiment may be two 0.010 inch membranes stacked together. An exemplary durometer hardness may be 55A and an exemplary slit length of 9 mm. Those skilled in the art will understand that the above are only exemplary and that the valve performance may be varied by altering the choice of materials for the membrane 32 (e.g., varying durometer and compression), a thickness of the materials and a size of the slit 34. In addition, if desired, additional stiffening members may be used for that purpose.

As shown in FIG. 1, the flow control membrane 32 is securely held in place within the housing 30, so that it will not be displaced by the force of the fluid flowing through the valve 20. For example, the flow control membrane 32 may be placed on a membrane seat 50 of the housing 30. The membrane 32 may, for example, be sandwiched between separable portions of the housing 30, so that a membrane retention portion 52 of the housing 30 applies a compressive force to a periphery of flow control membrane 32 thereby maintaining it in a desired position within the housing. However, if too strong a retention force is applied to a small surface portion of the membrane 32, the membrane 32 may be deformed possibly resulting in puckering or other deformation thereof. This may prevent the slit 34 from closing completely resulting in an insufficient seal and the many disadvantages associated therewith.

Too strong a compressive force applied to the membrane 32 may also cause stress cracks to form thereon at locations where the force is applied. Specifically, cracks may appear near a seating portion of the membrane 32 at which it is compressed between the membrane seat 50 and the membrane retention portion 52 of the housing 30. In the exemplary embodiment shown in the drawings, the seating portion is an annular region comprising a periphery of the flow control membrane 32. The housing may be formed by two halves, which are joined together to sandwich the flow control membrane 32 therebetween.

Furthermore, propagation of the slit (or slits) may result as strain concentrates at ends thereof when a fluid flows through the valve 20, forcing the slit 34 to the open configuration. If the membrane 32 is too thin, edges of the membrane 32 that are retained by the housing may not completely immobilize the membrane 32. The additional movement of the thin membrane 32 may cause further strains to be exerted on edges of the slit(s) 34, resulting in propagation of the slit and possible failure of the valve 20. This may cause the slit 34 to grow to a size whereby the resilience of the material of the membrane 32 is no longer able to maintain the edges of the slit 34 in contact with one another when subject to pressures below the threshold level.

Thus, from the standpoint of structural integrity it is desirable to form the flow control membrane 32 as thickly as possible to prevent deformation of the surface of the membrane 32 and to prevent cracks from propagating near the periphery of the membrane 32 and at the edges of the slit 34. However, the design of the flow control membrane 32 takes into consideration parameters in addition to structural strength. For example, a large flow rate through the valve 20 is desirable to minimize the time necessary to carry out procedures such as dialysis. As would be understood by those skilled in the art, the flow rate through a PASV valve is affected by the thickness of the flow control membrane 32, among other things. The thinner the membrane is made, the higher the rate of flow through the valve 20 as the slit 34 will open more widely for a given pressure applied thereto.

To satisfy these contradictory requirements a compromise is generally made by selecting a thickness of the membrane 32 which provides an acceptable structural reliability of the membrane 32 and at the same time allows sufficient flow of fluid therethrough. It is desired to enhance the structural integrity of the valve 20 while maintaining or increasing a flow rate therethrough for a given flow pressure.

Figure 2:
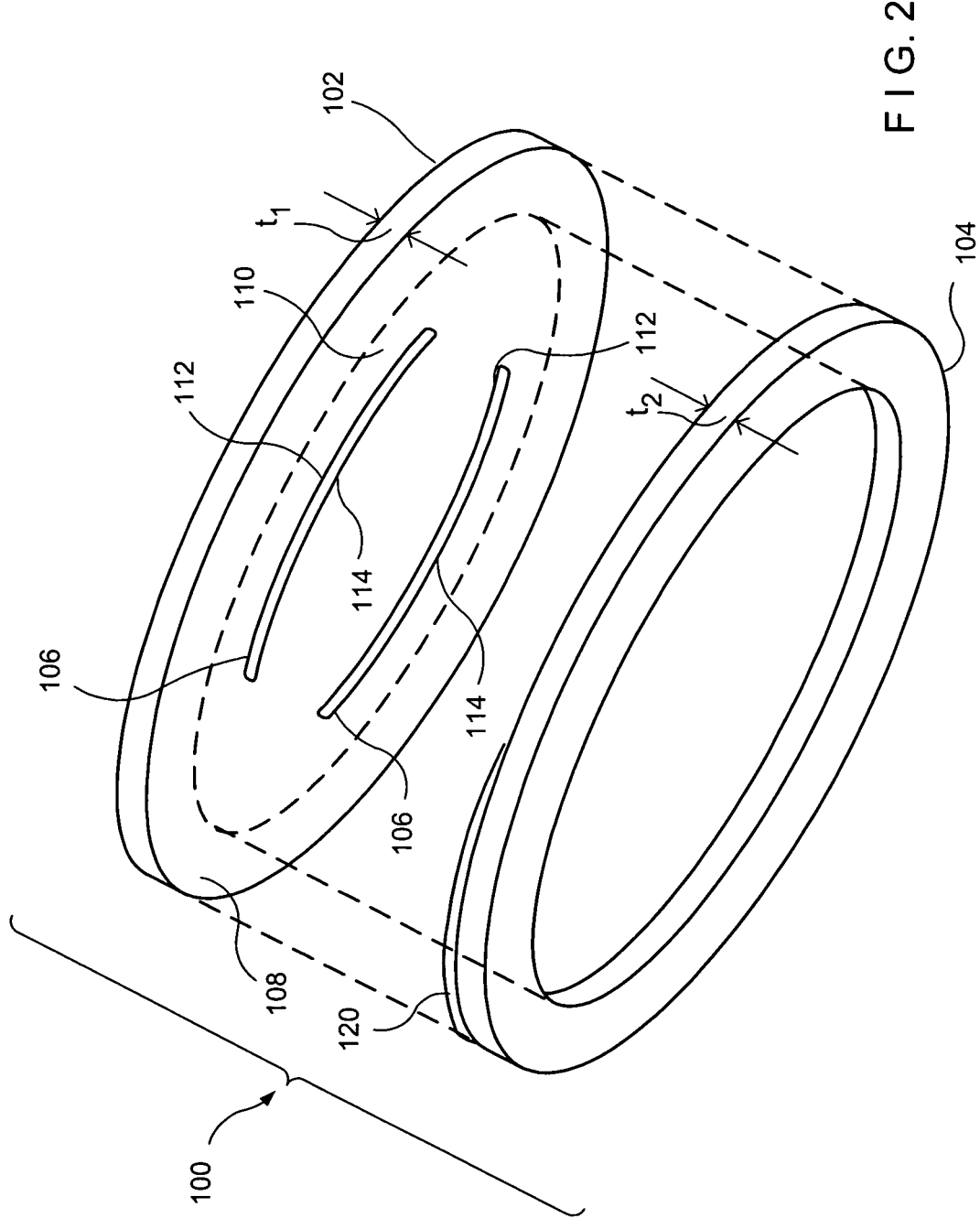
FIG. 2 is a perspective exploded view showing a stacked valve membrane according to an embodiment of the present invention.

Referring to FIG. 2 and according to the present invention, a stacked membrane is provided which satisfies in an optimal manner the two competing design goals of long structural life and high fluid flow rate. This result is achieved by using a thin flow control membrane 102 having one or more slits 106 extending therethrough to selectively impede the flow of a fluid through the valve 20. In this embodiment of the invention, the flow control membrane 102 is made as thin as necessary to achieve a desired flow rate therethrough at the expected pressure (e.g., the pressure applied by an operating dialysis machine). In addition to the thin membrane 102, a base membrane 104 is stacked thereon. The base membrane 104 is formed as desired to provide the extra strength necessary at the periphery of the thin membrane 102 to withstand the compressive forces exerted thereon. This base membrane 104 may preferably be made as thick as or thicker than the thin membrane 102. The base membrane 104 is preferably formed with a large opening formed in a center thereof so that a large portion of the thin membrane 102 is exposed while the seating portion to which the compressive forces are to be applied by the housing 30 is reinforced by the base membrane 104. The stacking order for the membranes 102, 104 may be changed, without affecting the properties of the resulting stacked membrane. Alternatively, the thin membrane 102 may be sandwiched between a pair of base membranes 104 for extra support.

By selecting an appropriate thickness for the base membrane 104, the resulting stacked membrane will have a greater thickness at locations where the retaining compressive force are exerted by the valve housing 30 while the portion of the stacked membrane surrounding the slits 106 is thinner to allow for a greater flow rate. Exemplary ranges for the thickness t1 and t2 as shown in FIG. 2 may be 0.005-0.1 inches. In addition, the base membrane 104 may be tapered to direct the flow of fluid into the valve.

More specifically, FIG. 2 shows a perspective view of a stacked membrane 100 of a PASV according to an embodiment of the present invention. As described above, the stacked membrane 100 comprises a flow control membrane 102 and a base membrane 104. The flow control membrane 102 is designed to extend across the flow chamber 36 of a valve housing 30, as shown in FIG. 1, in such a way that, when closed, it prevents the flow of fluids through the flow chamber 36. For example, a surface 110 of the flow control membrane 102 may have dimensions substantially equal to the cross sectional area of housing 30. Two curved slits 106 are formed in the exemplary flow control membrane 102, to selectively allow the passage of fluid therethrough. Opposing slit edges 112, 114 are joined when the stacked membrane 100 are maintained in the closed configuration through the natural bias of the material, so that no fluid passes therethrough. In one example, the resilient material forming the flow control membrane 102 applies a restoring force which urges edges 112, 114 to join. Alternatively, external resilient elements may be added to the membrane 102 in proximity to the slits 106, to urge the edges to join.

When the stacked membrane 100 is subject to a pressure via the fluids in the flow chamber 36 (e.g., pressure generated by an operating dialysis machine connected to the housing 30), of at least the threshold level, the edges 112, 114 are pushed apart against the restoring resilient force applied thereto, and the slits 106 open. As a result, the valve assumes the open configuration and flow is allowed to pass across flow control membrane 102. It will be apparent to those of skill in the art that different shapes, sizes, and configurations of one or more slits 106 may be used to allow fluid to flow across flow control membrane 102. The maximum flow through the stacked membrane 100 and the force required to open the slits 106 may be adjusted by adjusting the size and configuration of the slits, as well as by selecting appropriate dimensions of the flow control membrane 102 as would be understood by those of skill in the art. In an alternative embodiment, there may be multiple flow control membranes 102 that are stacked at a constant or variable spacing. In this embodiment, the base membrane 104 may be used as the outer most piece(s) of the multiple stack for the purpose of stiffening and reinforcement. Such an arrangement may be used to create inexpensive complex valves having spiral flows.

Figure 3:
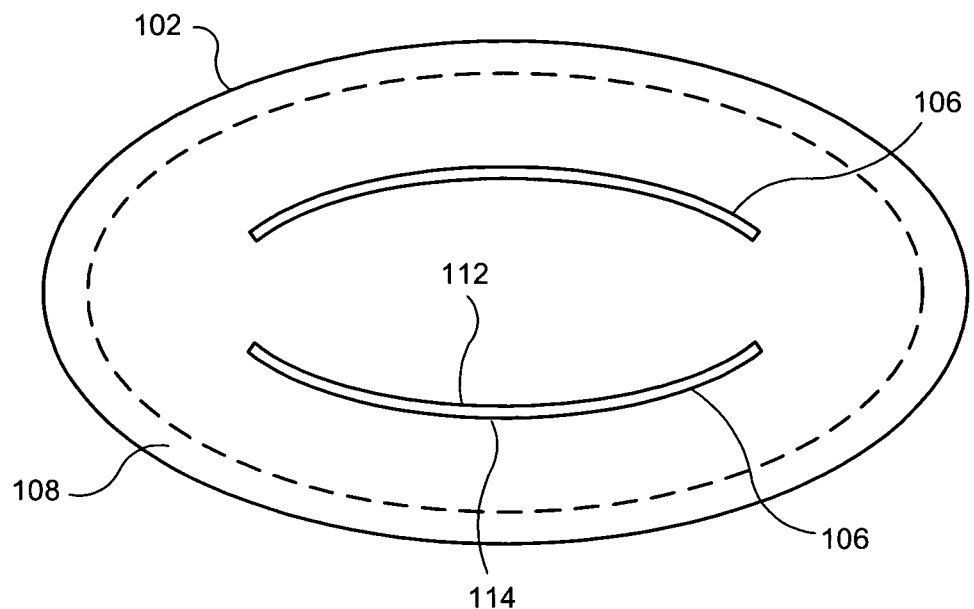
FIG. 3 is a top plan view of a flow control portion of the stacked valve membrane according to an embodiment of the present invention.

FIG. 3 shows a top elevation view of the flow control membrane 102. When mounted in a valve housing 30, the flow control membrane 102 rests on a membrane seat 50 as shown in FIG. 1. More specifically, a seating portion 108 of the membrane 102 is seated on the membrane seat 50, which is generally annular in shape. Accordingly, compression strains exerted by the housing 30 to retain the membrane 102 in place are concentrated on the seating portion 108, which in this exemplary embodiment is an annular region at the periphery of the membrane 102. As would be understood by those skilled in the art, different shapes and dimensions of the seating portion 108 may be selected, depending on the size and shape of the housing 30, and in particular on the size and shape of the membrane seat 50 and of the membrane holder 52. In one exemplary embodiment, the flow control membrane 102 may be elliptical, with a major axis of approximately 0.44 inches and with a minor axis of approximately 0.24 in. The seating portion 108 in this example takes up the annular periphery of the elliptical membrane in the range of 0.045-0.055 inches. These sizes and ranges are only exemplary and the size and selection of the seating portion is a function of the housing size and the slit size. The purpose is to create enough surface tension to help close the slit.

Figure 4:
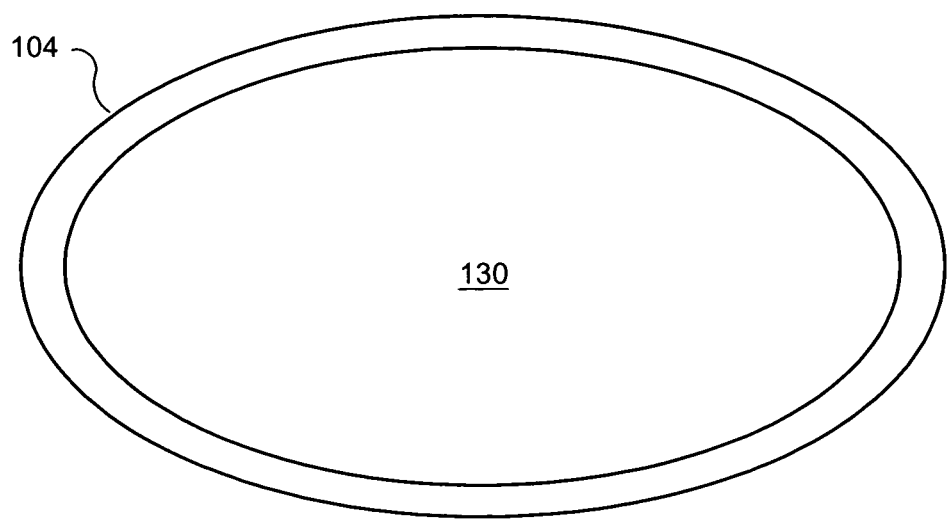
FIG. 4 is a top plan view of a base membrane portion of the stacked valve membrane according to the embodiment shown in FIG. 3.

A top elevation view of the base membrane 104 is shown in FIG. 4. As described above, the base membrane 104 is designed to form a region of the stacked membrane 100 which has a local thickness greater than a thickness of the flow control membrane 102. In the exemplary embodiment shown, the base membrane 104 has an outer periphery with dimensions that are substantially equal to the dimensions of the seating portion 108 of the flow control membrane 102. In this manner, the portion of stacked membrane 100 that is sandwiched between the retaining parts of the housing 30 is sufficiently thick to avoid the structural problems associated with thin membranes, as described above. In the exemplary embodiment, the base membrane 104 overlies the seating portion 108, which in turn overlies the membrane seat 50 of the housing 30. In different embodiments, the dimensions of the base membrane 104 may be different from those of the seating portion 108. However, the extent to which the base membrane 104 extends radially within the seating portion 108 is preferably minimized to prevent the flow rate from being reduced due to the resulting increase in the force acting to bias the flow membrane 102 toward the closed position. Of course, those skilled in the art will understand that this dimension may be altered to achieve a desired threshold pressure as well.

In the exemplary embodiment of FIG. 2, a thickness t1 of the flow control membrane 102 is substantially the same as a thickness t2 of base membrane 104. One advantage of this configuration is that the same initial membrane material may be used for both components of the stacked membrane 100, resulting in savings in the manufacturing process. For example, starting from the same membrane material, a conventional process may be used to form the slits 106 in the flow control membrane 102, while a stamping process may be used to cut out a center portion 130 of a similar membrane to form the annular base membrane 104 shown in the exemplary embodiment. Alternatively, the thickness t2 may be different from the thickness t1, and in particular may be greater to provide a greater increase in the structural strength of the stacked membrane 100. In one embodiment, both the base membrane 104 and the flow control membrane 102 may have a thickness of approximately 0.020 inches. With this configuration, the stacked membrane 100 allows passage of a fluid flow equivalent to that of a 0.020 inch thick membrane, but with the structural strength of a membrane of approximately twice that thickness.

The base membrane 104 and the flow control membrane 102 may be formed from any suitably strong and resilient material such as, for example, a polymeric material or silicone. Both membranes may be of the same material, or each may be formed of a separate composition. In one embodiment, an adhesive 120 is used to cement the membranes 102 and 104 together. For example, an RTV type polymer may be used for that purpose. It will be apparent to those skilled in the art that other methods of binding the flow control membrane 102 to the base membrane 104 may be used, and that the specific method may depend on the materials forming the two membranes 102, 104. In addition, the stacked membrane 100 may be assembled without adhesive (e.g., solvent bond, sonic weld, etc), so that the compression retentive force exerted by the housing on the stacked membrane maintains the two membranes 102, 104 in position relative to one another.

The stacked membrane 100 according to exemplary embodiments of the invention may be formed from two separate components, one of which is processed to have at least one slit extending therethrough, and the other of which may be annular extending around a periphery of the first component. For example, this annular shape may be obtained by removing a center of a substantially circular or elliptical membrane. Alternatively, the base membrane 104 and the thin membrane 102 may be formed integrally by extrusion of a thin membrane with a thick edge to produce a single piece stacked membrane 100. However, the extrusion process for a complex membrane may be more demanding and expensive than the above-described two piece process. Quality control for the two piece process may also be less demanding as it may be easier to inspect a flat, uniform membrane (prior to forming the slits or stamping the center) than it is to inspect a more complex membrane with multiple thicknesses.

The present invention has been described with reference to specific embodiments, more specifically to a stacked membrane having two slits and an annular base membrane, as used in a dialysis catheter PASV. However, other embodiments may be devised that are applicable to other types of pressure actuated valves, which have different configurations of slits and different shapes of the base membrane, without departing from the scope of the invention. Accordingly, various modifications and changes may be made to the embodiments without departing from the broadest spirit and scope of the present invention as set forth in the claims that follow. The specification and drawings are accordingly to be regarded in an illustrative rather than restrictive sense.

What is claimed is:

1. A pressure activated valve for a vascular access catheter, comprising:
a hub for introducing fluid to or removing fluid from the vascular access catheter, the hub comprising:
a housing having a proximal end and a distal end, the housing being comprised of:
a first portion and a second portion;
a lumen extending from the proximal end of the housing to the distal end of the housing, the lumen being substantially cylindrical and allowing for fluid to flow into and out of the vascular access catheter;
a membrane seat located within the lumen of the housing and adjacent the distal end of the housing;
a flow control membrane including a plurality of non-intersecting slits, and a seating portion located along a periphery of the flow control membrane, wherein the seating portion is configured to engage the membrane seat of the housing, situating the flow control membrane adjacent the distal end of the housing; and
a resilient annular base member comprising of a different thickness than the flow control membrane, the different thickness being thicker than the flow control membrane, the base member having an outer periphery that aligns with the seating portion of the flow control membrane and the membrane retention portion of the housing, the resilient annular base member being stacked either on a top surface of the seating portion of the flow control membrane or on a bottom surface of the flow control membrane such that the resilient annular base member and membrane seat contact opposite and equal portions of a periphery of the flow control membrane, the resilient annular base member being a separate component from the flow control membrane,
wherein the plurality of non-intersecting slits open when subjected to a fluid pressure of at least a predetermined threshold level.

2. A pressure activated valve according to claim 1, wherein the flow control membrane portion has a thickness of no more than 0.035 in.

3. A pressure activated valve according to claim 1, wherein a thickness of the flow control membrane is between 0.005 and 0.100 inches.

4. A pressure activated valve according to claim 1, wherein the combined thickness of the resilient annular base member and the flow control membrane is between 1 and 20 times a thickness of the flow control membrane.

5. A pressure activated valve according to claim 1, wherein the resilient annular base member and the flow control membrane comprise the same material.

6. A pressure activated valve according to claim 1, wherein the resilient annular base member and the flow control membrane comprise silicone.

7. A pressure activated valve according to claim 1, wherein the resilient annular base member overlays the seating portion such that a thickness of the periphery of the flow control membrane is increased.

8. A pressure activated valve according to claim 1, wherein the resilient annular base member is overlaid at a spacing established by a thickness of the flow control membrane.

9. A pressure activated valve according to claim 1, wherein the flow control membrane is placed between a pair of resilient annular base members.

10. A pressure activated valve for a vascular access catheter, comprising:
a hub for introducing fluid to or removing fluid from the vascular access catheter, the hub comprising:
a housing having a proximal end and a distal end, the housing being comprised of:
a first portion and a second portion;
a lumen extending from the proximal end of the housing to the distal end of the housing, the lumen being substantially cylindrical and allowing for fluid to flow into and out of the vascular access catheter;
a membrane seat located within the lumen of the housing and adjacent the distal end of the housing;
a flow control membrane including a plurality of non-intersecting slits, and a seating portion located along a periphery of the flow control membrane, wherein the seating portion is configured to engage the membrane seat of the housing, situating the flow control membrane adjacent the distal end of the housing; and
a resilient annular base member comprising of a different thickness than the flow control membrane, the base member having an outer periphery that aligns with the seating portion of the flow control membrane and the membrane retention portion of the housing, the resilient annular base member being stacked either on a top surface of the seating portion of the flow control membrane or on a bottom surface of the flow control membrane such that the resilient annular base member and membrane seat contact opposite and equal portions of a periphery of the flow control membrane, the resilient annular base member being a separate component from the flow control membrane, the resilient annular base member and flow control membrane together having a thickness of up to 0.1 inch,
wherein the plurality of non-intersecting slits open when subjected to a fluid pressure of at least a predetermined threshold level.

11. A pressure activated valve according to claim 10, wherein the flow control membrane is placed between a pair of resilient annular base members.

12. A pressure activated valve for a vascular access catheter, comprising:
a hub for introducing fluid to or removing fluid from the vascular access catheter, the hub comprising:
a housing having a proximal end and a distal end, the housing being comprised of:
a first portion and a second portion;
a lumen extending from the proximal end of the housing to the distal end of the housing, the lumen being substantially cylindrical and allowing for fluid to flow into and out of the vascular access catheter;

a membrane seat located within the lumen of the housing and adjacent the distal end of the housing;

a flow control membrane including a plurality of non-intersecting slits, and a seating portion located along a periphery of the flow control membrane, wherein the seating portion is configured to engage the membrane seat of the housing, situating the flow control membrane adjacent the distal end of the housing; and a resilient annular base member comprising of a different thickness than the flow control membrane, the base member having an outer periphery that aligns with the seating portion of the flow control membrane and the membrane retention portion of the housing, the resilient annular base member being stacked either on a top surface of the seating portion of the flow control membrane or on a bottom surface of the flow control membrane such that the resilient annular base member and membrane seat contact opposite and equal portions of a periphery of the flow control membrane, the resilient annular base member being tapered, the resilient annular base member being a separate component from the flow control membrane, wherein the plurality of non-intersecting slits open when subjected to a fluid pressure of at least a predetermined threshold level.

13. A pressure activated valve according to claim 12, wherein the flow control membrane is placed between a pair of resilient annular base members.

* * * * *